United States Patent [19]

Ball

[11] Patent Number: 4,546,794
[45] Date of Patent: Oct. 15, 1985

[54] GAS MIXING APPARATUS

[75] Inventor: Graham J. Ball, Great Dunmow, England

[73] Assignee: The BOC Group plc, London, England

[21] Appl. No.: 556,210

[22] Filed: Nov. 29, 1983

[30] Foreign Application Priority Data

Dec. 1, 1982 [GB] United Kingdom ............... 8234188

[51] Int. Cl.⁴ ........................................... G05D 11/03
[52] U.S. Cl. .................................... 137/599; 137/607; 128/200.19; 128/203.12
[58] Field of Search .............................. 137/607, 599; 128/200.19, 203.12, 203.25

[56] References Cited

U.S. PATENT DOCUMENTS

| | | | |
|---|---|---|---|
| 2,921,605 | 1/1960 | Booth et al. | 137/607 X |
| 3,351,057 | 11/1967 | Goodyear et al. | 128/203.12 X |
| 3,875,968 | 4/1975 | Olofsson et al. | 137/607 X |
| 4,266,573 | 5/1981 | Braatz | 137/607 X |

FOREIGN PATENT DOCUMENTS 492052 9/1938 United Kingdom ............... 137/607

*Primary Examiner*—Martin P. Schwadron
*Assistant Examiner*—Stephen M. Hepperle
*Attorney, Agent, or Firm*—Roger M. Rathbun; Larry R. Cassett

[57] ABSTRACT

A gas mixing apparatus in the form of an anaesthesia apparatus includes a first path for oxygen, a second path for nitrous oxide and third path for carbon dioxide. The first path is divided for at least a part of its length into first and second by-pass passages 210, 212. A valve 214 in the first by-pass passage 210 is inter-connected with a valve 222 controlling the flow of a nitrous oxide through the second path and a valve 215 in the second by-pass passage 212 is interconnected with a valve 232 controlling the flow of carbon dioxide through the third path. The interconnecting means 250, 260 are so arranged that the opening of the valves 222, 232 associated with the second and third paths causes corresponding opening of the valves 214, 215 associated with the by-pass passages such that the total flow of oxygen through the apparatus will never fall below a predetermined minimum proportion by volume.

9 Claims, 5 Drawing Figures

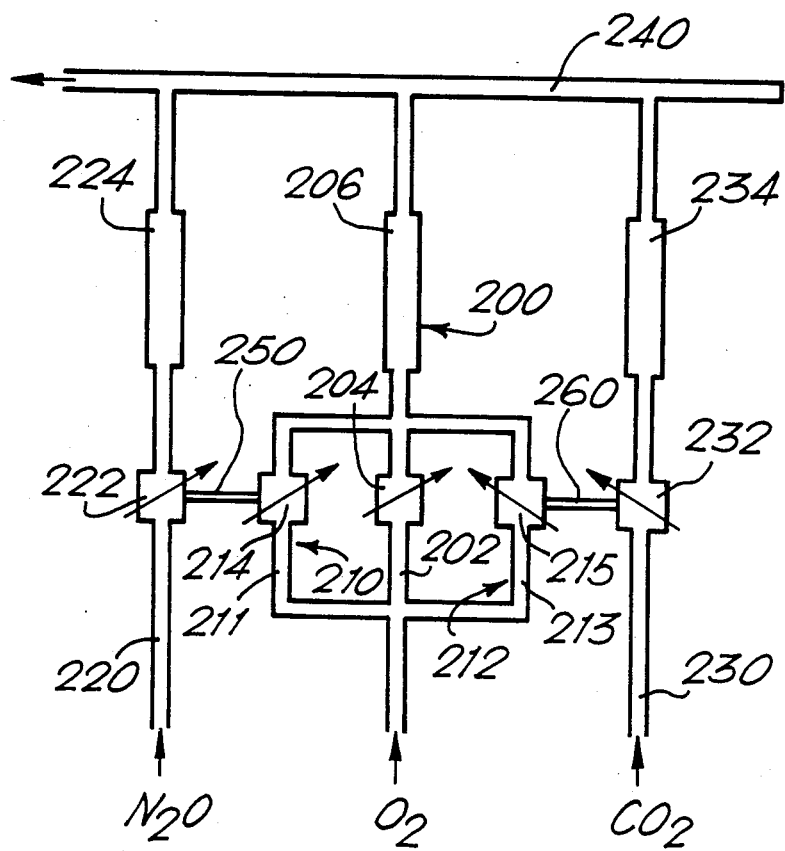

GAS MIXING APPARATUS

The present invention relates to gas mixing apparatus and in particular to anaesthesia apparatus in which at least three separate gases or gas mixtures are delivered to the anaesthesia apparatus and then mixed in predetermined proportions before delivery to a patient.

It is known from U.S. Pat. No. 4,266,573, for an anaesthesia apparatus to provide a mixture of oxygen and another gas, usually nitrous oxide, in predetermined proportions for administration to a patient. This known apparatus includes two needle valves each controlling the flow of oxygen and nitrous oxide respectively to a common outlet. The needle valves are interconnected by a "lost motion" mechanism such that when the needle valve controlling the nitrous oxide is opened it will, after a predetermined movement, open the needle valve controlling the oxygen. Furthermore, the interconnection is such that by closing the needle valve controlling the oxygen this will after a predetermined movement also start to close the needle valve controlling the nitrous oxide.

The advantage of this known anaesthetic apparatus is that it ensures the delivery to a patient of a respirable gas mixture in terms of oxygen sufficiency at all settings of the needle valves.

However, it suffers from the disadvantages that should a third gas or gas mixture be required for delivery to a patient then the proportion of oxygen in the finally delivered gas mixture might well drop below the predetermined lower limit with consequent dangerous results.

For the avoidance of doubt the use of the term "gas" throughout this specification is intended to cover "gas mixtures" for example air, where applicable.

It is an aim of the present invention to provide a gas mixing apparatus for the mixing of at least three gases which will ensure that the proportion of one of said gases in the mixture will never reduce below a predetermined level.

More particularly, it is an aim of the present invention to provide an anaesthesia apparatus which can provide a mixture of oxygen and at least two other gases to a patient and in which the delivery to the patient of an oxygen deficient mixture is prevented.

According to the present invention, a gas mixing apparatus for providing a gas mixture containing at least first, second and third gases, the proportion by volume of the first gas in the gas mixture being maintained above a predetermined lower limit comprises first, second and third paths respectively for the passage therethrough of said first, second and third gases towards a common mixing means, the second and third paths each including a valve for controlling the flow of its respective gas therethrough, the first path being divided for at least a part of its length into at least first and second by-pass passages, each including a valve for controlling the flow of the first gas therethrough, first means interconnecting the valve associated with the first by-pass passage with the valve associated with the second path and second means interconnecting the valve associated with the second by-pass passage with the valve associated with the third path, the first and second interconnecting means both being arranged so that movement to open either of the valves associated with the second and third paths will also cause the valves associated with the first and second by-pass passages respectively to open to prevent the percentage of the first gas by volume falling below a predetermined proportion.

Preferably, the first gas is oxygen, the second gas is nitrous oxide and the third gas is carbon dioxide and in that a flowmeter is included in each path down stream of its associated valve(s), the by-pass passages rejoining the first path upstream of the flowmeter associated with the first path.

Embodiments of the invention will now be described by way of example, reference being made to the Figures of the accompanying diagrammatic drawings in which:

FIG. 5 is a schematic diagram of a further gas mixing apparatus.

Figure 1:
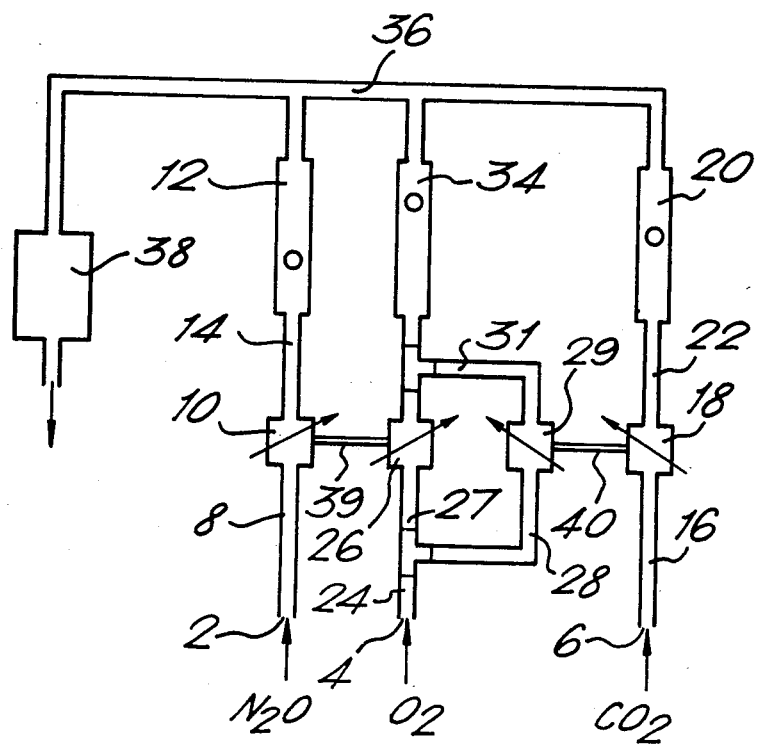
FIG. 1 is a schematic diagram of a gas mixing apparatus.

As shown in FIG. 1, a gas mixing apparatus in the form of an anaesthesia apparatus includes three different paths for the passage therethrough of three different gases, namely, oxygen, nitrous oxide and carbon dioxide.

The first path for oxygen includes an inlet 4 and two by-pass passages 24, 28 arranged in parallel each including respectively a conduit 27, 31 and a needle valve 26, 29. The conduits 27, 31 join at a position upstream of a common flowmeter 34. The second path for the nitrous oxide includes an inlet 2, conduit 8, needle valve 10, conduit 14 and flowmeter 12. The third path for the carbon dioxide includes an inlet 6, conduit 16, needle valve 18, conduit 22 and flowmeter 20.

All three paths terminate at a common mixing means in the form of a mixing conduit 36 which leads to a vaporizer 38.

Proportioning means 39 interconnects the needle valve 10,26 and proportioning means 40 interconnects needle valves 29,18 as will be explained.

Figure 2:
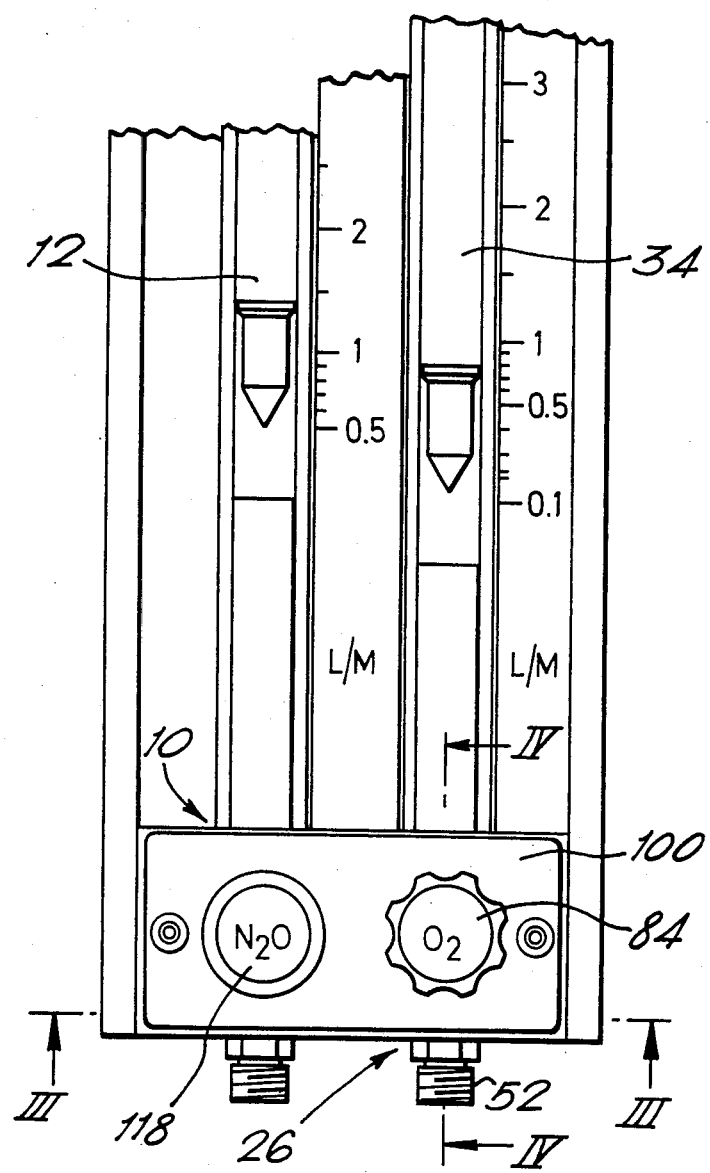
FIG. 2 is a partial front view of the gas mixing apparatus of FIG. 1 illustrating valves controlling the flow of two gases through the gas mixing apparatus.
Figure 3:
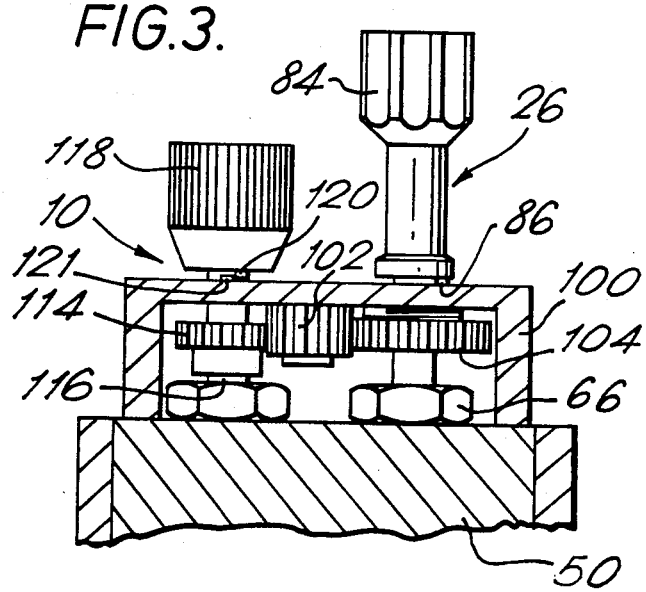
FIG. 3 is a cross-section on line III—III of FIG. 2.
Figure 4:
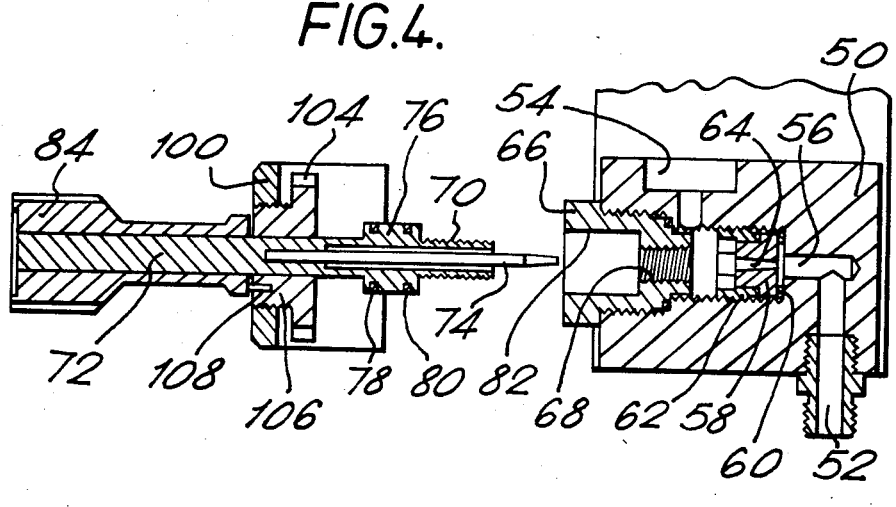
FIG. 4 is an exploded cross section on the line IV—IV of FIG. 2.

Referring also to FIGS. 2, 3 and 4, the pair of interconnected valves 10,26 with their proportioning means 39 will now be described in detail.

The needle valves 10,26 are mounted on a manifold block 50. The manifold block 50 has an inlet 52 and an outlet 54 interconnected by a passageway 56 for the passage therethrough of oxygen and a similar inlet, outlet and passageway (not shown) for the passage therethrough of nitrous oxide.

Attached to but spaced from the manifold block 50 is a bridge piece 100. Mounted centrally on the bridge piece 100 is an idler gear 102. Immediately to the right of the idler gear 102 (as seen in FIG. 3) and meshing therewith is a gear 104 having a boss 106 which is screw threaded for engagement within a screw threaded hole in the bridge piece 100. Protruding leftwards (as shown in FIG. 4) from the boss 106 is a coupling pin 108.

The passageway 56 has an enlarged threaded portion occupied in part by a valve seat 58 that seals against an O-ring 60. The valve seat 58 has a tapered through hole 64 and is secured in the passageway 56 by a screw bush 62. Also secured to the manifold block 50 is a sleeve 66 having an internal threaded portion 68. The portion 68 receives the threaded shank 70 of a spindle 72 carrying a valve stem 74. The spindle 72 has an embossment 76 carrying O-rings 78,80 which engage in a sealing manner the surface of a counterbore 82 in the sleeve 66.

The spindle 72 passes with a free fit through the gear 104 and, at its left hand end (as shown in FIG. 4) it carries a control knob 84 having a lug 86 (see FIG. 3) for engaging the coupling pin 108 in a manner to be described.

Immediately to the left (as shown in FIG. 3) and meshing with the idler gear 102 is a gear 114 which is secured to a spindle 116 of the needle valve 10. On the side of the bridge piece 100 remote from the manifold block 50 is a control knob 118 which is attached to the spindle 116. The knob 118 carries a lug 120 which is arranged to engage a stop pin 121 extending from the bridge piece 100 towards the knob 118 in a manner to be described.

The remainder of the needle valve 10 including the spindle 116 is substantially the same as already described with reference to the needle valve 26 and for succinctness will not be described further.

In operation, turning control knob 84 anti-clockwise will cause the spindle 72 to move to the left (as shown in FIG. 4) and permit the passage of oxygen from inlet 52 through passage 56 to outlet 54. Turning the knob 84 clockwise will have the reverse effect in that it will cause the spindle 72 to move to the right (as shown in FIG. 4) thereby causing the valve stem 74 to enter the tapered hole 64 in the valve seat 58 and thereby prevent or inhibit the passage of oxygen through the passage 56.

The same is true of the control knob 118 which when turned anti-clockwise will permit the passage of nitrous oxide through the manifold block 50 and when turned clockwise will inhibit the flow of nitrous oxide through the manifold block 50.

If both valves 10 and 26 are fully closed then, in this condition, the lug on each knob 84 and 118 is arranged to engage in a clockwise sense against its respective coupling pin 108 and stop pin 21. If the valve 26 is opened by rotating the knob 84 anti-clockwise then the lug 86 on the knob 84 separates from the coupling pin 108 on the gear boss 106 and describes a spiral path that will carry it clear of the coupling pin 108 at each successive full turn. Thus, any chosen flow rate of oxygen may be freely set without any rotation being communicated to the gear 104.

If the nitrous oxide control knob 118 is rotated anti-clockwise instead of the knob 84 then it rotates the nitrous oxide spindle 116 and with it gear 114. The rotational movement of the gear 114 is transmitted via the idler gear 102 which cauases the gear 104 to rotate. The coupling pin 108 extending from the gear boss 106 describes a spiral path and being already registered against the lug 86 on the knob 84 applies a driving torque to the knob 84 and thus to the spindle 72 which makes the spindle 72 rotate and open the valve 26. In this manner, an oxygen flow rate is produced automatically on opening the nitrous oxide valve 10. If the nitrous oxide valve 10 is opened further the oxygen valve 26 will continue to be opened according to the ratio of the gears 114 and 104.

Should the nitrous oxide control knob 118 turned clockwise to close the valve 10 then the coupling pin 108 parts company spirally from the lug 86 on the knob 84 and will therefore pass under the lug 86 without engaging it after one or more revolutions of closure. Thus the oxygen flow rate will remain unchanged while the nitrous oxide flow rate will be reduced. The clockwise rotation of the nitrous oxide knob 118 is stopped by the fixed stop pin 121 when the valve 10 is fully closed.

If the knob 84 is turned anti-clockwise for more oxygen flow then the lug 86 disengages from the coupling pin 108 and will remain clear of it. The nitrous oxide flow setting will remain unchanged.

Finally, if the oxygen control knob 84 is turned clockwise to reduce oxygen flow then the reverse situation obtains to that of turning the nitrous oxide control knob 118 anti-clockwise and the nitrous oxide valve spindle 116 is made to rotate thereby reducing the nitrous oxide flow through the manifold block 50.

However, the proportioning means 40 is different in that the valves 18, 29 are directly geared together throughout their respective ranges of rotation. Only one control knob is provided which is on valve 18. The ratio of the gearing interconnecting the two valves 18,29, is such that when opening or closing valve 18 by means of the control knob, valve 29 is concomitantly opened and closed to ensure thereby that the proportion of oxygen flowing through valve 29 never falls below a predetermined minimum level.

It should be noted, that in the embodiment described above, four needle valves 10, 26, 29, 18, are provided.

Referring now to FIG. 5, a gas mixing apparatus in the form of an anaesthesia apparatus again includes three different paths for the passage therethrough of three gases, for example, oxygen, nitrous oxide and carbon dioxide.

The first path for the oxygen includes a central passage 200 comprising conduit 202, needle valve 204 and flowmeter 206; and two by-pass passages 210, 212, each including respectively a conduit 211, 213 and a needle valve 214, 215. The conduits 211, 213 rejoin the conduit 202 upstream of the flowmeter 206. The second path for the nitrous oxide includes a conduit 220, needle valve 222 and flowmeter 224. The third path for the carbon dioxide includes a conduit 230, needle valve 232 and flowmeter 234.

All three paths terminate at a common mixing means in the form of a mixing conduit 240.

Proportioning means 250 interconnects valves 222, 214 and proportioning means 260 interconnects valves 232, 215.

In this embodiment, the proportioning means are substantially the same in that associated needle valve 222, 214; 232, 215 are respectively geared together throughout their ranges of rotation. A control knob on valve 222 enables valve 222 to be opened or closed and the gearing causes a concomitant opening or closing of valve 214. Similarly, the control knob on valve 232 enables valve 232 to be opened or closed and the gearing causes a concomitant opening or closing of valve 215. Again, the ratio of the gearing interconnecting the pairs of valves 222, 214; 232, 215 is such that the proportion of oxygen flowing through the by-pass passages 210, 212 never falls below a predetermined minimum level. However, to ensure that, if necessary, pure oxygen can be delivered to a patient, needle valve 204 is provided in the central passage 200, which valve is independent of any interconnecting means and has its own control knob.

It should be noted that whilst five needle valves, namely valves 222, 214, 204, 215 and 232 are provided, that is one more than with the embodiment previously described, some simplification in manufacturing is obtained due to the direct gearing of the proportioning means 250, 260, which is less complex than the proportioning means 39 described with reference to the previous embodiment.

Referring back to the embodiment described and illustrated in FIGS. 1 to 4, in a modification, exactly the same relationship and mode of operation could exist with the needle valve 18, 29 and proportioning means 40 as with the needle valves 10, 26 and proportioning means 39. Furthermore, proportioning means using a chain and sprockets for the "lost motion" effect as described in U.S. Pat. No. 4,266,573 could replace either one or both the proportioning menas 39, 40 described with reference to this embodiment.

It will be appreciated that, although apparatus with separate paths for three different gases, namely oxygen, nitrous oxide and carbon dioxide, have been described, four or even more paths for separate gases could be provided.

If for example a fourth path for a fourth gas were provided in the embodiment illustrated in FIG. 5, this would also entail the provision of a further by-pass path for the oxygen, so that a needle valve on the further by-pass path could be interconnected by proportioning means with a needle valve on the fourth path.

A particular advantage of the embodiments described above is that, regardless of the settings of the needles valves controlling the nitrous oxide and carbon dioxide, the total flow of oxygen through the apparatus will never fall below a predetermined lower level. If that lower level is set at 21% or above of the total volume of the gas mixture delivered to a patient, then the patient will always have a respirable mixture of gas delivered to him.

I claim:

1. A gas mixing apparatus for providing a gas mixture containing at least first, second and third gases, the proportion by volume of the first gas in the gas mixture being maintained above a predetermined lower level, comprising first, second and third paths respectively for the passage therethrough of said first, second and third gases towards a common mixing means, the second and third paths each including a rotatable needle valve for controlling the flow of its respective gas therethrough, the first path being divided for at least a part of its length into at least first and second by-pass passages, each including a rotatable needle valve for controlling the flow of the first gas therethrough, first means interconnecting the needle valve associated with the first by-pass passage with the needle valve associated with the second path and second means interconnecting the needle valve associated with the second by-pass passage with the needle valve associated with the third path, the first and second interconnecting means both being arranged so that rotational movement to open either of the needle valves associated with the second and third paths will also cause the needle valves associated with the first and second by-pass passages respectively to rotate to open to prevent the percentage of the firs gas by volume falling below a predetermined proportion.

2. A gas mixing apparatus as claimed in claim 1, in which the valve associated with the second path has a control knob for opening and closing said valve, said valve being geared to the valve associated with the first by-pass passage, and the ratio of the gearing being such that movement of the control knob to open or close said valve will concomitantly cause the valve associated with the first by-pass passage to be opened or closed to prevent the percentage of the first gas by volume falling below a predetermined proportion.

3. A gas mixing apparatus as claimed in claim 1 or 2 in which the valve associated with the third path has a control knob for opening and closing said valve, said valve being geared to the valve associated with the second by-pass passage, and the ratio of its gearing being such that movement of the control knob to open or close said valve will concomitantly cause the valve associated with the second by-pass passage to be opened or closed to prevent the percentage of the first gas by volume falling below a predetermined proportion.

4. A gas mixing apparatus as claimed in claim 3 in which the first path includes a central passage which has a valve arranged in parallel with the valves associated with the by-pass passages, said valve having a control knob for controlling the flow through the central passage of said first gas.

5. A gas mixing apparatus as claimed in claim 1, in which the valve associated with the second path and the valve associated with the first by-pass passage each have a control knob for opening and closing the respective valves, the first interconnecting means including gearing which permits closure of the valve associated with the second path, whilst allowing the valve associated with the first by-pass passage to remain open, but opening of the valve associated with the second path causes the concomitant opening of the valve associated with the first by-pass passage to thereby prevent the percentage of the first gas by volume falling below a predetermined proportion.

6. A gas mixing apparatus as claimed in claim 1 or 5, in which the valve associated with the third path and the valve associated with the second by-pass passage each have a control knob for opening and closing the respective valves, the second interconnecting means including gearing which permits closure of the valve associated with the third path whilst permitting the valve associated with the second by-pass passage to remain open, but opening of the valve associated with the third path causes a concomitant opening of the valve associated with the second by-pass passage, thereby to prevent the percentage of the first gas by volume falling below a predetermined proportion.

7. A gas mixing apparatus as claimed in claim 1, in which at least the first interconnecting means includes a lost motion mechanism whereby the second valve is limited to a predetermined flow of the second gas after which further opening of the second valve also causes the valve associated with the first by-pass passage to open to prevent the percentage of the first gas by volume falling below a predetermined proportion.

8. A gas mixing apparatus as claimed in claim 1, in which the first gas is oxygen, the second gas is nitrous oxide and the third gas is carbon dioxide and in that a flowmeter is included in each path downstream of its associated valve (s) the by-pass passages rejoining upstream of the flowmeter associated with the first path.

9. A gas mixing apparatus as claimed in claim 8, in which the common mixing means is a conduit and in that outlets from each flowmeter communicate with said conduit.

* * * * *